United States Patent [19]

Goldstein et al.

[11] Patent Number: 5,026,991

[45] Date of Patent: Jun. 25, 1991

[54] GASEOUS SPECIES ABSORPTION MONITOR

[75] Inventors: Neil Goldstein, Medford; Fritz Bien, Concord; Lawrence Bernstein, Lexington, all of Mass.

[73] Assignee: Spectral Sciences, Inc., Burlington, Mass.

[21] Appl. No.: 410,106

[22] Filed: Sep. 20, 1989

[51] Int. Cl.⁵ ..................... G01N 21/17; G01N 21/59
[52] U.S. Cl. .................... 250/343; 250/339; 250/341; 356/317
[58] Field of Search .............. 250/343, 339, 341; 356/317; 372/28

[56] References Cited

U.S. PATENT DOCUMENTS

| | | | |
|---|---|---|---|
| 3,431,514 | 3/1969 | Oshman et al. | 372/32 |
| 3,586,997 | 6/1971 | Kinsel | 372/18 |
| 3,700,891 | 10/1972 | Luft | 250/343 |
| 4,101,847 | 7/1978 | Albanese | 372/31 |
| 4,410,273 | 10/1983 | Mantz et al. | 356/319 |
| 4,674,091 | 6/1987 | Colson | 372/20 |
| 4,730,112 | 3/1988 | Wong | 250/343 |

OTHER PUBLICATIONS

Kemeny et al., "Utilization of Tunable Infrared Diode Lasers for the Determination of Labelled Molecules in Gas Mixtures", Acta Physica Academiae Scientiarum Hungaricae, Tomus (vol.) 48, (No.) 1, (1980), pp. 93–102.

Primary Examiner—Constantine Hannaher
Assistant Examiner—Jacob M. Eisenberg
Attorney, Agent, or Firm—Iandiorio & Dingman

[57] ABSTRACT

A wavelength-locked laser gaseous species monitor including a variable wavelength laser with a laser output actively stabilized to a wavelength at or near an absorption wavelength of the species being monitored. The laser is modulated about that wavelength to establish a modulated output with a known frequency and bandwidth. The modulated output is passed through the sample being monitored and then collected. An even harmonic of the collected output with respect to the modulation frequency is determined, and the presence in the sample of the species being monitored is detected from the even harmonic signal.

24 Claims, 5 Drawing Sheets

GASEOUS SPECIES ABSORPTION MONITOR

This invention was made with government support under Contract No. ISI-8760819 awarded by the National Science Foundation. The government has certain rights in the invention.

FIELD OF INVENTION

This invention relates to a gaseous species absorption monitor and more particularly to such a monitor which modulates a laser output about the central wavelength of an absorption line of the species of interest and determines an even harmonic of the laser output transmitted through a gas sample with respect to the modulation frequency to detect the presence in the sample of that species.

BACKGROUND OF INVENTION

Several optical absorption measurement techniques have been proposed for gaseous species monitoring and quantification. One technique irradiates a sample with a broadband frequency source and disperses the transmitted light with a device such as a diffraction grating. The dispersed light is then monitored for the presence of a characteristic absorption line of the species of interest. However, in gas mixtures the absorption lines of the different species are often closely spaced. If they are, it is extremely difficult to disperse the light finely enough to have sufficient resolution to detect the single line of interest. Thus, the dispersal technique does not allow the monitoring of many gas mixtures, which prevents the dispersal monitors from having universal application. Even if the absorption line can be distinguished, the device used to disperse the light is typically complex and costly. Thus, optical gaseous species monitors employing radiation dispersal techniques have limited utility, and are typically very costly.

Some of the problems created by the use of a broadband source have been alleviated by the substitution of a narrow band laser source. Single or multiple mode semiconductor diode lasers having bandwidths which may be approximately the same width as an absorption line have been employed as the radiation source in optical absorption species monitors. One such technique is disclosed in U.S. Pat. No. 4,730,112. The wavelength of the source is typically slowly scanned by varying the laser drive current through a range of wavelengths including the absorption line of interest. The absorption line is then found by the detection of an intensity dip in the transmitted radiation. The species concentration may be determined by measuring the intensity decrease, which may be accomplished by comparing the amount of incident radiation to the amount of transmitted radiation; the greater the absorption, the greater the species concentration. However, this technique does not disclose any means for compensating for variations in absorption depth due to changes in line width associated with pressure and temperature variations. Thus, the reference apparatus has relatively limited utility.

The patented technique has three inherent difficulties which are typical of such scanning techniques. First, it is difficult to identify the absorption of interest and determine its exact magnitude when other absorption features are present in the spectral scan. Therefore such techniques have limited application in cases where there are other possible interfering absorptions within the spectral scan. Second, because the laser must be scanned over a large wavelength range, the sample species absorption is only observed a small fraction of the time. Therefore, detection sensitivity in the narrow band containing the absorption of interest and capabilities for real time monitoring of the sample species are limited. Only changes which occur on a time scale much longer than that of a single scan can be detected. Third, most available laser sources have instabilities in the output wavelength which result in spurius absorption measurements and distort the absorption line shape. These limit the accuracy of a scanning measurement. For gallium aluminum arsenide lasers such as those used in the patented device, these instabilities limit detection sensitivity in a scanning mode.

Because of the inherent difficulties, the scanning technique is suitable only for a limited set of sample species and conditions, such as oxygen monitoring at atmospheric pressure. Application to a larger range of monitoring conditions requires a technique which can accurately determine sample concentrations for weak absorbers with variable absorption line widths; the scanning technique measures only the absorption strength at the line center, and does not include a method to determine concentration in cases where pressure or temperature variations can alter the absorption line width and peak absorption strength.

SUMMARY OF INVENTION

It is therefore an object of this invention to provide a gaseous species absorption monitor that is extremely sensitive.

It is a further object of this invention to provide such a monitor that has an extremely short response time and is capable of real-time monitoring.

It is a further object of this invention to provide such a monitor that is relatively simple and inexpensive.

It is a further object of this invention to provide a laser source monitor that does not scan the laser across a broad wavelength band.

It is a further object of this invention to provide such a monitor which employs harmonic detection techniques to provide the means for determining concentration, line width, and sample pressure and temperature.

This invention results from the realization that laser-source gaseous species absorption monitors can be dramatically improved by locking the laser wavelength on the center of an absorption wavelength of the species being monitored, modulating the laser about that central point, and determining an even harmonic of the laser light transmitted through the sample with respect to the laser modulation frequency to detect the concentration of the species of interest.

This invention features a wavelength-locked laser gaseous species monitor with a variable wavelength laser for providing a laser output and means for adjusting the central wavelength of the laser output to a first laser wavelength at or near a first absorption line wavelength of the species being monitored. The monitor also includes means for modulating the laser output about the first laser wavelength to establish a first modulated output having a first modulation frequency and bandwidth. There are means for providing the modulated output to a sample being monitored and means for collecting the modulated output transmitted through the sample. The monitor further includes means for determining an even harmonic of the collected output with respect to the modulation frequency, and means, responsive to the means for determining, for detecting from the harmonic signal the presence in the sample of the species being monitored. Preferably, the even harmonic is the second harmonic.

In a preferred embodiment, the absorption monitor further includes means, responsive to the means for determining the even harmonic, for resolving the concentration of the species in the sample. In that case, the means for modulating may further establish a second modulated output having the first modulation frequency and a second modulation bandwidth. The means for resolving the concentration may then include means for comparing the even harmonics of the first and second collected outputs. Preferably, one of the modulation bandwidths is at least as large as the line width of the absorption line of the species being monitored. In another alternative embodiment, the monitor further includes means for determining the line width of the absorption line. In that case, the line width may be determined by comparing the even harmonics.

The means for adjusting the central wavelength of the laser output may include a reference cell, which may contain the species being monitored or a species with a line proximate the line being monitored. In that case, there is preferably further included means for providing the modulated output to the reference cell and means for collecting the modulated output transmitted through the reference cell. The means for adjusting the laser wavelength may further include means for determining an odd harmonic of the collected reference cell output with respect to the modulation frequency. To accomplish this, a drive signal is preferably provided to the laser having a wavelength proportional to the odd harmonic for driving the central laser output to match that of the absorption line being monitored.

Preferably, the laser includes a semiconductor diode laser. The means for adjusting the wavelength of the laser output may include means for controlling the temperature and/or the supply current of the laser. In an alternative preferred embodiment, the monitor includes means for determining the temperature of the sample. That may be accomplished by including means for adjusting the central wavelength of the laser output to a second laser wavelength at or near a second absorption wavelength of the species being monitored. Further included may be means for modulating the laser output about the second laser wavelength to establish a third modulated output having the first modulation frequency and bandwidth. In that case, the third modulated output may be provided to the sample, the output transmitted to the sample may be collected, and the even harmonic of the third collected output with respect to the modulation frequency may be determined. The means for determining the temperature of the sample may then include means for comparing the even harmonics of the collected outputs.

DISCLOSURE OF PREFERRED EMBODIMENT

Other objects, features and advantages will occur from the following description of a preferred embodiment and the accompanying drawings, in which.

This invention may be accomplished in a wavelength-locked laser gaseous species absorption monitor having a variable wavelength laser and means for adjusting the laser output to a wavelength at or near an absorption wavelength of the species being monitored. The laser is modulated about that central wavelength to establish a modulated output with a known modulation frequency and bandwidth. The modulated output is passed through a sample being monitored, and an even harmonic of the radiation passed through the sample with respect to the modulation frequency is determined to detect the presence in the sample of the species being monitored. The monitor may also be used to determine the concentration of the species, the line width of the absorption line, and the sample pressure and temperature.

Figure 1:
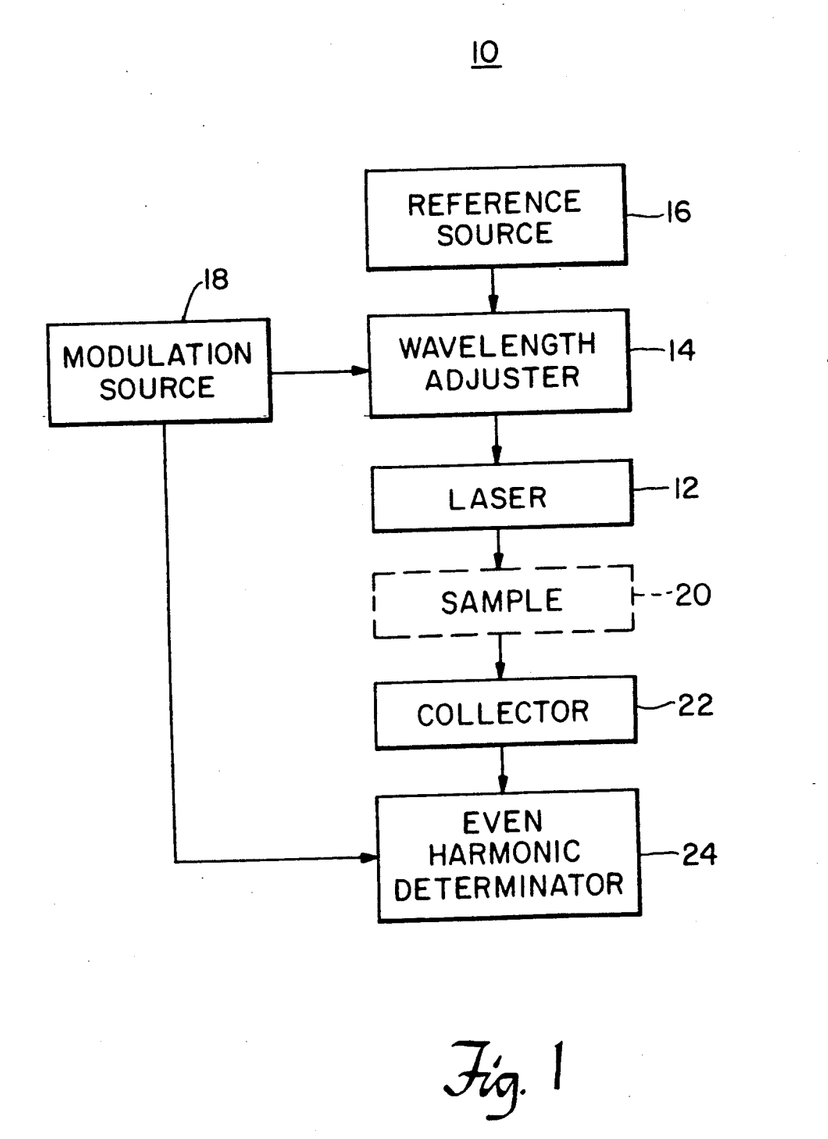
FIG. 1 is a schematic diagram of the gaseous species absorption monitor according to this invention.

There is shown in FIG. 1 wavelength-locked laser gaseous species absorption monitor 10 according to this invention. Monitor 10 includes laser 12 which may be a semiconductor diode laser, for example, a gallium aluminum arsenide diode. The output of laser 12 is passed through sample 20 and collected by collector 22. Even harmonic determinator 24 is employed to detect the presence in sample 20 of the species being monitored.

To detect the presence of a gaseous species being monitored, it is necessary to choose in advance at least one absorption line for that species. The output of laser 12 is adjusted by wavelength adjuster 14 to have a wavelength at or near that absorption line. Preferably, a line is chosen which is not immediately adjacent to a line of another species which may be present in the sample to enable the accurate determination of the presence of a species.

Wavelength adjuster 14 is responsive to reference source 16 and modulation source 18. Reference source 16 is employed to drive the laser output to a predetermined wavelength at or near the chosen absorption line. Preferably, the output of laser 12 is driven to be centered on that line. Wavelength adjuster 14 may alter the drive current supplied to laser 12 to vary its output wavelength, as is more fully explained below in connection with FIG. 2.

Once laser 12 is operating at or near the absorption wavelength, it is modulated about that central wavelength by modulation source 18. The modulated laser output is passed through sample 20 and the collected output is passed to even harmonic determinator 24, which is also responsive to modulation source 18. Determinator 24 determines an even harmonic of the collected radiation with respect to the modulation frequency to detect the presence of the species being monitored.

Figure 2:
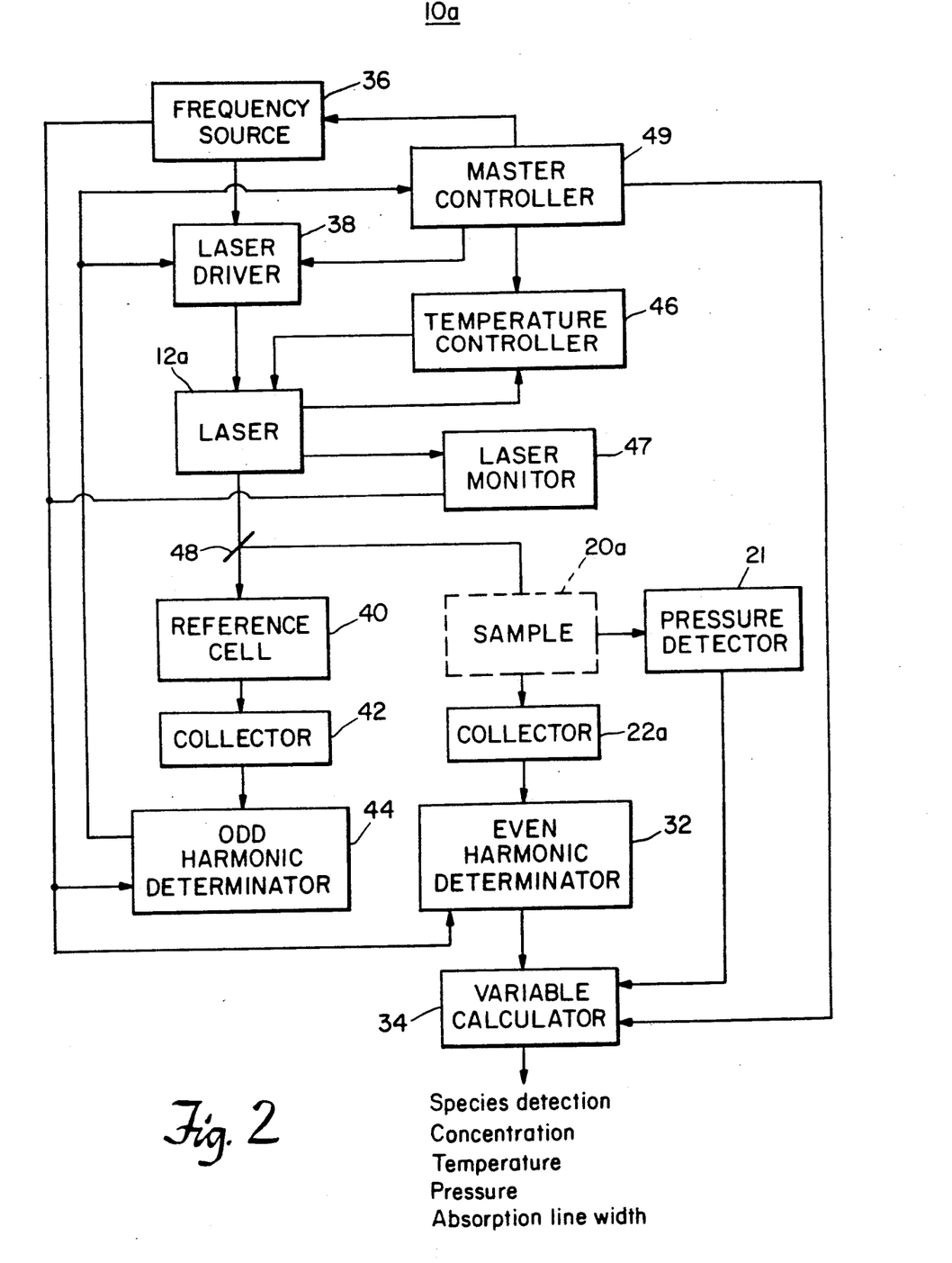
FIG. 2 is a more detailed schematic diagram of the gaseous species absorption monitor of FIG. 1.

A more detailed embodiment of the monitor according to this invention is shown in FIG. 2. Monitor 10a includes laser 12a, whose output is passed through beam splitter 48 to supply its radiation to both reference cell 40 and sample 20a. Laser monitor 47 supplies a signal representative of the laser intensity to harmonic determinators 32 and 44 for normalization of the signals from collectors 42 and 22a. Pressure detector 21 supplies a signal representative of the sample pressure to variable calculator 34 as will be explained below.

The wavelength of laser 12a is a function of its junction temperature. This temperature is controlled by temperature controller 46 in conjunction with the current from laser driver 38, which may supply a variable current output to alter the laser wavelength. Controller 46 is preferably used to maintain the laser wavelength in near coincidence with the chosen absorption line. In that case, fine adjustment of the wavelength is made on the millisecond time scale by adjusting with the signal from determinator 44 the carrier current supplied by driver 38 to laser 12a.

Frequency source 36 supplies a high frequency, preferably a radio frequency, signal to laser driver 38. The output of laser driver 38 is then the sum of a dc current for driving laser 12a at a wavelength at or near the absorption wavelength of the species being monitored, and a sinusoidally varying current with an established frequency and amplitude, which results in modulation of the laser wavelength over a predetermined bandwidth. Master controller 49 establishes nominal operating values for laser driver 38, temperature controller 46, and frequency source 36. Preferably, the laser temperature and dc drive current are adjusted to drive laser 12a to a central wavelength coincident with that of the chosen absorption line. The modulation bandwidth of the laser is chosen for each application as is described below, but is typically of the order of the absorption line width.

The modulated output from laser 12a is passed through reference cell 40 containing a reference species, which may be the species being monitored, and sample 20a, which is the sample being monitored. Sample 20a may be contained in a separate flow-through cell, not shown, for real-time monitoring. If sample 20a is remote, the laser radiation may be directed to the sample by fiber optic cables. Collectors 42 and 22a may be photodiodes which collect at least part of the laser radiation passed through reference cell 40 and sample 20a, respectively, and provide a signal representative of the transmitted laser intensity to harmonic determinators 44 and 32, respectively. Determinators 44 and 32 are also responsive to frequency source 36 for determining an harmonic of the collected laser output with respect to the modulation frequency.

Frequency source 36 supplies a high frequency sinusoidal signal to laser driver 38 as described above. The signal supplied by frequency source 36 to odd harmonic determinator 44 is preferably a square wave signal having a frequency which is an odd integer multiple of the frequency of the modulation signal supplied to driver 38. Preferably, the frequency is three times the modulation frequency and sixty degrees offset therefrom as is further described below. Frequency source 36 also supplies a square wave signal an even integer multiple of the modulation signal frequency to even harmonic determinator 32. Preferably, that signal has twice the frequency of the laser modulation signal and is offset forty-five degrees therefrom, as is also further described below.

Laser driver 38 is responsive to odd harmonic determinator 44, which may be a phase sensitive amplifier, for completing the feedback loop through reference cell 40. The signal from determinator 44 is used in conjunction with laser driver 38 to drive the output from laser 12a so that its wavelength matches the central wavelength of the absorption line of the species being monitored. In order to accomplish this feedback control, the wavelength of laser 12a must initially be set by controller 49 to be close enough to the absorption line so that the bandwidth of the modulated signal encompasses at least part of that absorption line. If the initial laser wavelength is so far from the absorption line that there is no overlap, no feedback signal will be generated by determinator 44, and the laser will not be driven to lock on the central wavelength of the absorption line of interest. Thus, it is necessary to choose in advance an absorption line to be monitored, and enable master controller 49, in conjunction with laser driver 38 and temperature controller 46, to drive laser 12a to initially radiate at a wavelength relatively close to that absorption line.

Even harmonic determinator 32, which may also be a phase sensitive amplifier, is employed to detect the presence in sample 20a of the species of interest. Determinator 32 is responsive to the radiation passed through sample 20a and the square wave signal at twice the modulation frequency generated by frequency source 36. As described below, the detection of an even harmonic signal indicates the detection of an absorption line coincident to the absorption line of the species being monitored. Thus, the development of an even harmonic signal indicates the detection in sample 20a of the species of interest. The signal from determinator 32 may also be passed to variable calculator 34 for determining species concentration, sample temperature and pressure, and absorption line width as is further described below.

Figure 3A:
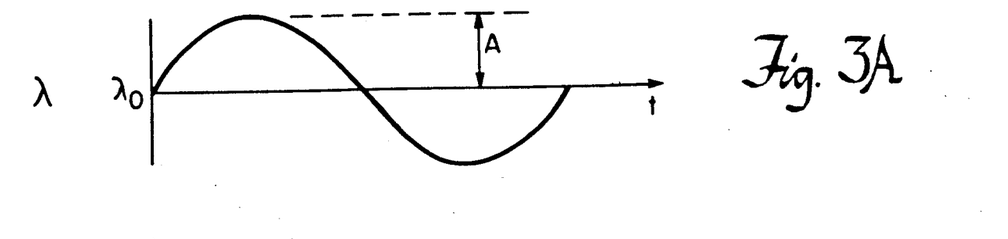
FIGS. 3A-3D are graphical depictions of an example of a laser wavelength modulation, the incident and detected waveform, and the second and third harmonics of the gaseous species absorption monitor according to this invention.
Figure 3B:
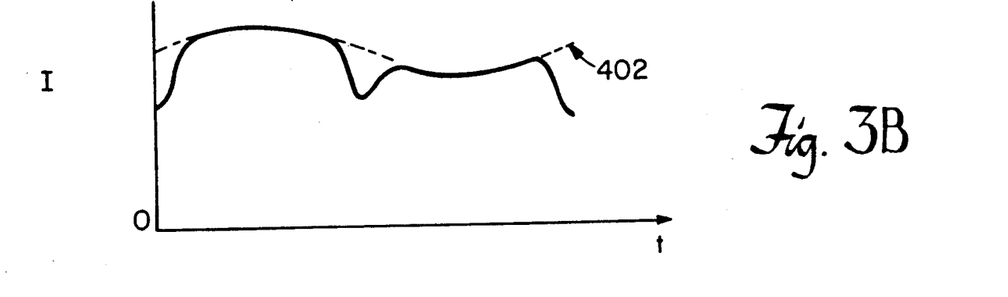
Figure 3C:
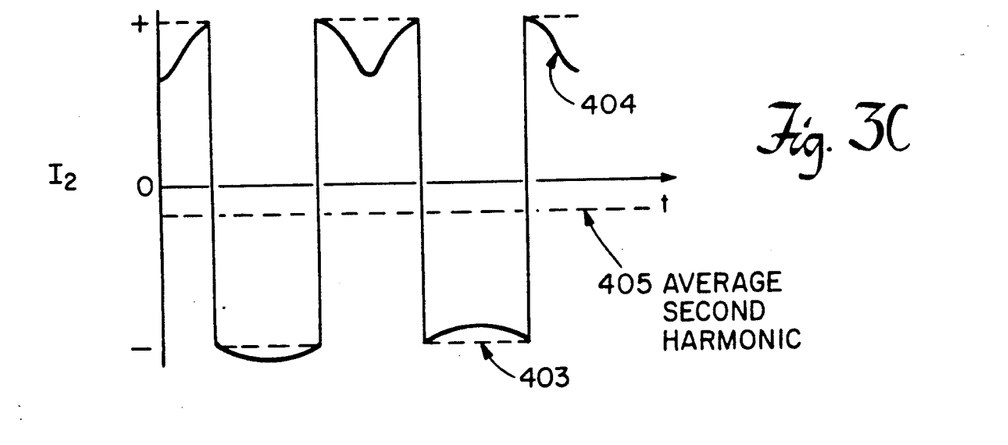
Figure 3D:
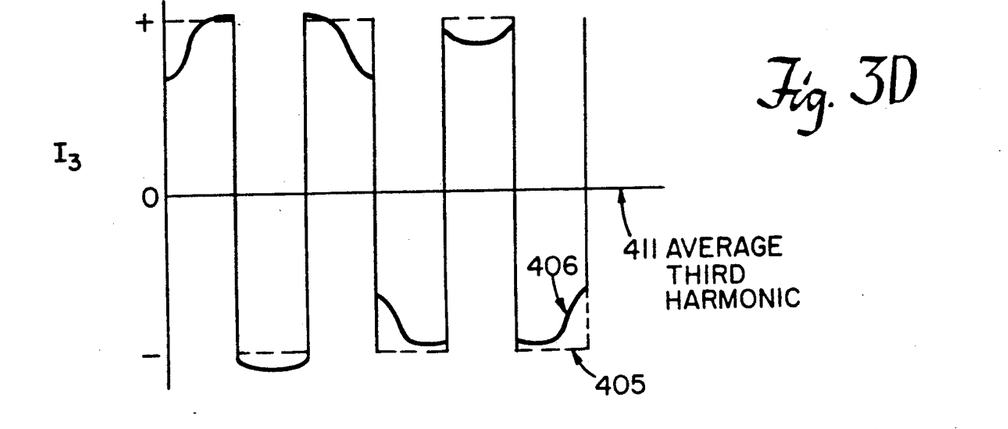
Figure 4A:
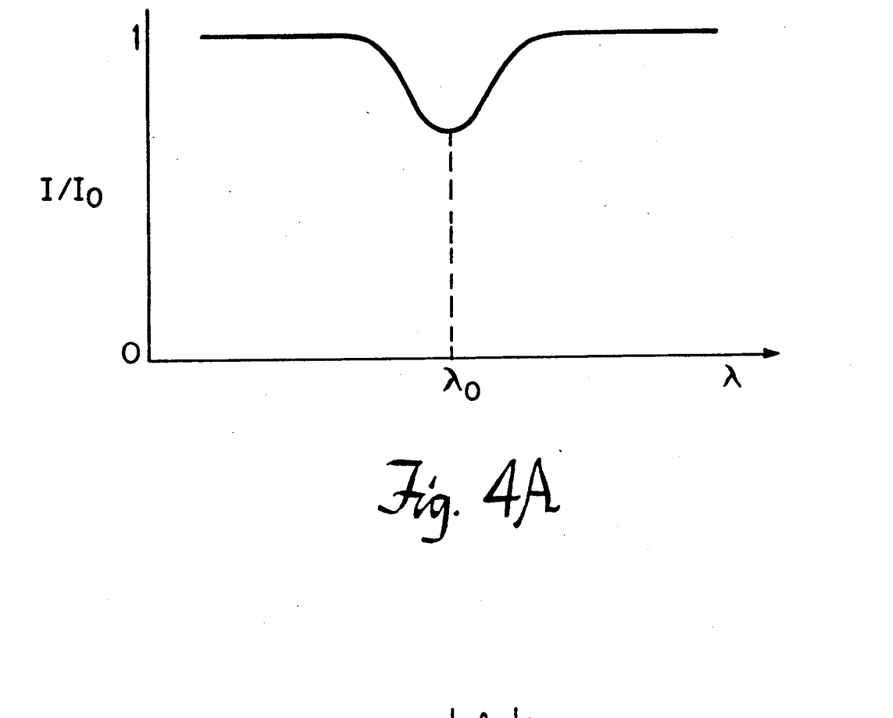
FIGS. 4A and 4B are exemplary graphical depictions of an absorption line and the dependence of the third harmonic signal on the laser central wavelength.
Figure 4B:
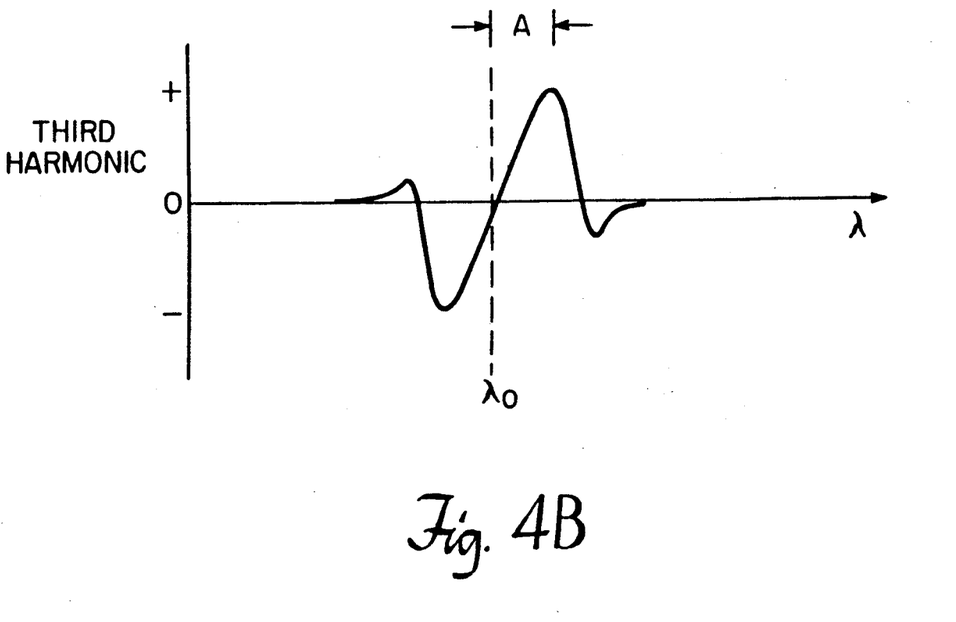
Figure 5A:
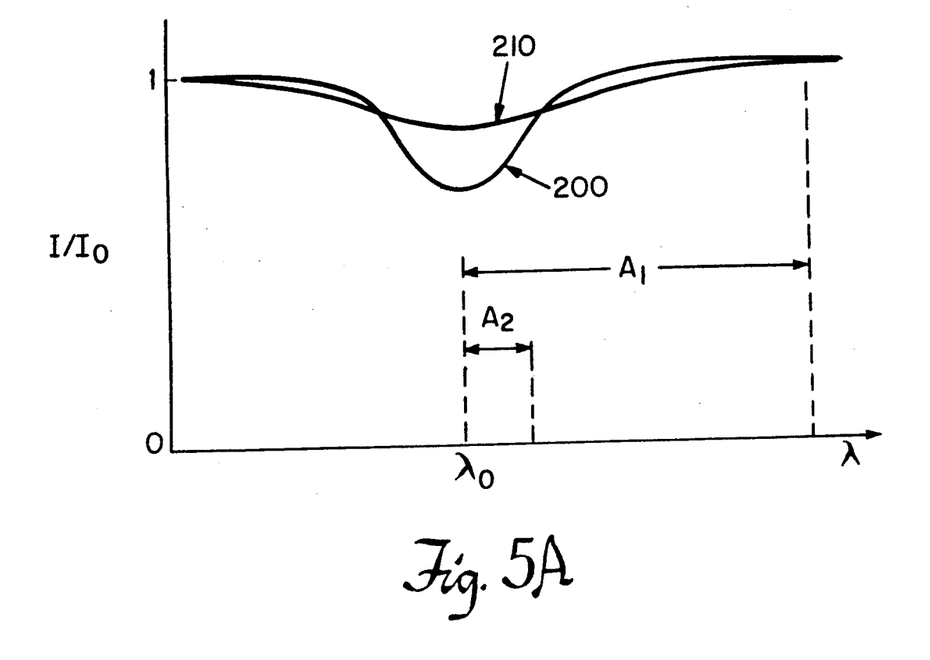
FIGS. 5A and 5B are graphs of the normalized laser sample signal for two different line widths, and the dependence of the second harmonic signal on modulation amplitude for the absorption monitor according to this invention.
Figure 5B:
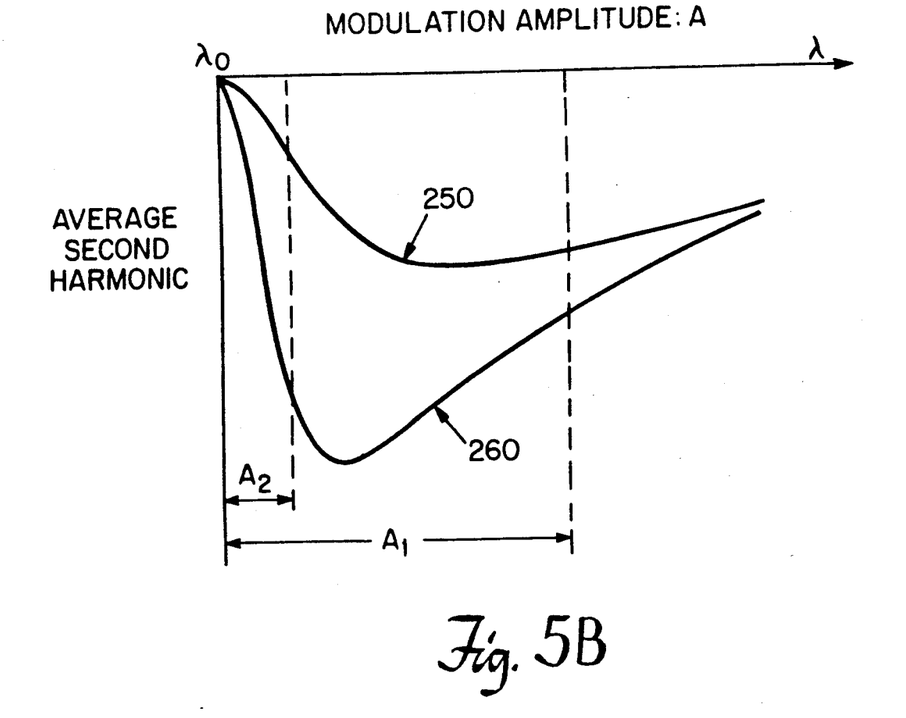

FIGS. 3 through 5 are used to illustrate the basic principles of operation of the gaseous species monitor of this invention locked to the center of a molecular absorption line. FIG. 3 depicts the means of generation of the second and third harmonic signals used in quantifying the absorption and controlling the laser frequency. FIG. 4 depicts the mechanism of line locking using the third harmonic signal. FIG. 5 depicts the means of determining absorber concentration from the observed second harmonic signals.

The methods of generation of second and third harmonic signals are well understood by those skilled in the art. This process is described graphically in FIGS. 3A through 3D for the specific case of a laser locked to the center of an absorption line of interest. FIG. 3A depicts the wavelength modulation of the laser output through one modulation cycle. The laser wavelength is varied sinusoidally with amplitude A over a bandwidth 2A which is centered on the maximum of the absorption line. In this example, the amplitude has been chosen to be much larger than the line width.

FIG. 3B depicts the corresponding intensity I of the light incident on collector 22a after passing through sample 20a containing the absorber of interest. Also shown is the incident radiation, $I_o$, indicated by dashed line 402. The absorption, which appears as a decrease in the transmitted intensity, occurs twice per cycle. The transmitted intensity, I, also contains a component that is sinusoidally modulated at a frequency f which results from the intensity modulation of the laser which accompanies the wavelength modulation shown in FIG. 3A. Signal I is passed to determinator 32, FIG. 2.

Determinator 32 produces the second harmonic signal by multiplying the detected radiation times a multiplier signal indicated by curve 403, FIG. 3C. This multiplier signal is a square wave of frequency $2f$, or twice the laser drive frequency, offset as shown. The resulting signal $I_2$ is shown by curve 404 in FIG. 3C. Averaging this signal over time results in the second harmonic signal. In this case the absorption occurs at the center of the laser wavelength modulation bandwidth where the square wave multiplier has a positive value. Therefore, the averaged second harmonic signal has a negative value; shown as curve 405 in FIG. 3C. A maximum negative value for the second harmonic occurs when the central laser wavelength is coincident with the absorption line of interest. The final signal from determinator 32, FIG. 2, consists of the average second harmonic normalized to the input radiation, $I_o$. The generation of a signal from determinator 32 indicates the detection of the species of interest.

The analogous third harmonic signals from determinator 44, FIG. 2, are shown in FIG. 3D. The laser output detected after passing through reference cell 40 is multiplied by squarewave 405 from frequency source 36 at three times the laser modulation frequency f. The resulting signal, $I_3$, curve 406, reverses sign at each zero crossing. As a result, when the central laser wavelength is coincident with the absorption line, the time averaged third harmonic signal is zero, as shown by curve 411, FIG. 3D. In that case, the feedback signal from odd harmonic determinator 44 to laser driver 38 is zero and the central laser wavelength is kept on the center of the absorption line.

The wavelength of laser 12a will tend to drift slightly with time. However, the feedback signal from odd harmonic determinator 44 adjusts the laser frequency virtually instantaneously as it starts to drift. Thus, the feedback signal keeps the central laser wavelength locked on the center of the absorption line being monitored.

The mechanism of the laser line locking is illustrated in FIGS. 4A and 4B. FIG. 4A depicts the absorption line to which the laser is locked. The laser is modulated with an amplitude A which in this case has been made equal to the line width for illustrative purposes. The laser normally operates with a central wavelength equal to the line center $\lambda_o$. FIG. 4B depicts the value of the average third harmonic signal determined by determinator 44 as the laser central wavelength is displaced from the line center. It should be understood that in operation the absorption monitor is not scanned through the absorption line. Rather, the laser is modulated about the center of the absorption line as described above.

When the central laser wavelength is coincident with the absorption line, the integrated third harmonic feedback signal is zero. As the central laser wavelength moves below the center of the absorption line, the integrated third harmonic signal becomes negative. Since the laser wavelength is inversely proportional to its drive current, the negative integrated third harmonic signal is employed directly as a feedback signal to decrease the laser drive current to drive the laser wavelength back to be coincident with the absorption line. Conversely, as the central laser wavelength moves past the absorption line, the integrated third harmonic signal fed back to the laser driver increases the laser current to decrease the wavelength back to that of the absorption line. Thus, the use of the integrated third harmonic signal as a feedback signal automatically drives the laser output to be coincident with that of the absorption line in the reference cell.

In most cases the gaseous species in the reference cell is the same as that being monitored in the sample cell. However, the reference cell may contain an alternative species with a near coincident absorption wavelength; it is only necessary to insure that the modulation is large enough to overlap at least partially the line of interest. Depending on the presence of interfering lines, the reference line could be as much as half a wave number from the line being monitored. This feature allows the monitor to be used on species which can not be held in a reference cell, for example unstable species. It is only necessary to employ a species with an absorption line close to the line being monitored.

The third harmonic signal may also be used to establish laser operation on or near a preselected absorption line. As the third harmonic signal is determined in a reference cell with known conditions, the magnitude of the third harmonic signal can be used by controller 49, FIG. 2, as a means of verification of the identity of the selected absorption line. In the preferred embodiment the absorption line is selected by employing controller 49 to adjust the temperature and drive current of the laser diode to match preselected values which closely correspond to an absorption wavelength in the reference cell. The laser current and/or modulation amplitude A is rapidly adjusted until the third harmonic is observed. The odd harmonic output of determinator 44 is then applied to driver 38, and the laser is locked to the absorption wavelength.

The absolute concentration of the gaseous absorber species in the sample cell is determined from the average second harmonic signals developed in determinator 32. In all cases, the concentration is directly proportional to the average second harmonic signal. The proportionality constant is uniquely determined by the relative size of the absorption line width and modulation amplitude A. If the line width is constant and known, the concentration may be determined by multiplying the second harmonic by the appropriate proportionality constant. In other applications, the line width is unknown and can vary with pressure or sample composition. In these applications, both the absorption depth and line width are uniquely determined by a series of second harmonic measurements obtained with different modulation amplitudes. These are in turn converted to the output variable of interest, which may be concentration, sample composition, pressure, or line width. This process is illustrated below for two representative cases.

For most atmospheric trace gas monitoring, the line width is essentially constant with concentration. If a line is chosen with little or no line strength temperature dependence and the sample pressure is known, for example by use of pressure detector 21, FIG. 2, the average second harmonic signal at a single modulation bandwidth is sufficient to determine species concentration; the second harmonic signal is proportional to concentration.

Generally, concentration equals the average second harmonic value times a constant K, which is uniquely determined from the second harmonic ratio at two modulation amplitudes. However, if the line width is unknown, but known to be much smaller than the modulation amplitude, K is independent of line width and measurement at a single modulation amplitude is sufficient.

For a more general case of species detection, the absorption line width varies in a well understood fashion with temperature, pressure, and gas composition of the sample being monitored. In that case the line width and absorption strength can be simultaneously measured and used to determine absorber concentration in the sample. This is done by comparison of the second harmonic signal obtained at two or more modulation amplitudes, as illustrated in FIGS. 5A and 5B.

FIG. 5A shows the laser light intensity transmitted through sample 20a for two different pressure broadened samples with identical absorber density, but different line widths. Curve 200 results from a low pressure sample with a smaller line width, and curve 210 results from a high pressure sample with a large line width. Note that the integral of absorption with respect to wavelength over the entire absorption line is independent of line width and is the same in both cases.

The second harmonic signals associated with each of these samples are plotted as a function of modulation amplitude in FIG. 5B. Curve 260 corrsponds to the small line width absorption shown in curve 200. Curve 250 corresponds to the large line width absorption shown in curve 210. Two measurements with modulations $A_1$ and $A_2$ are sufficient to uniquely determine the concentration and line width. In that case, controller 49 is enabled to drive frequency source 36 to alter the modulation amplitudes as desired. Large modulation amplitude $A_1$ corresponds to the case illustrated in FIG. 3. Virtually all the absorption line occurs near the center of the laser modulation, and is summed with positive sign to form the average second harmonic. Therefore, the second harmonic signal measure for amplitude $A_1$ is nearly proportional to the integrated absorption, which is the same for both samples. Small modulation amplitude $A_2$ is approximately equal to the line widths. In this case there is substantial absorption near the furthest extent of modulation, and the second harmonic is a sensitive indicator of sample line width.

A series of measurements such as these uniquely determines the concentration over a large range of pressure and temperature conditions. In general, a unique calibration can be achieved if one of the two modulation amplitudes is approximately equal to the sample line width.

Extensions of this technique to more than two modulation amplitudes will allow additional applications as will be evident to those skilled in the art. These include, but are not limited to: detailed measurements of spectral line shapes, applications over extended pressure ranges, and calibration of absorption when the laser is locked to a reference gas with an absorption wavelength which is different than that of the sample gas. Controller 49 supplies the appropriate drive information to calculator 34 to enable calculation of the desired variable.

Variable calculator 34 may be used to calculate the desired quantity such as sample concentration or sample pressure. All measurable quantities are functions of the absorption strength and line shape, and can be determined by comparison on the observed second harmonic signals to those calculated from known spectrometric constants which can be readily predetermined for each specific absorption line.

In the most general case, in which the sample temperature is not known, the absorption monitor of this invention may be employed to measure temperature. To do that, at least two different absorption lines with different temperature dependence are chosen in advance. The central laser wavelength may be moved from one line to the other by master controller 49 in conjunction with laser driver 38 and temperature controller 46. Alternatively, a second laser which radiates at the second absorption line, not shown, may be employed. In either case, the integrated absorption is determined for both absorption lines as described above and the temperature is calculated by variable calculator 34; the sample temperature is directly related to the ratio of the integrated absorptions of the two lines. As a result, the gaseous species absorption monitor of this invention may be employed to detect and determine the concentration of almost any gaseous species under almost any condition, whether or not the sample temperature is known.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A wavelength-locked laser gaseous species monitor, comprising:
   variable wavelength laser means for providing a laser output;
   means for adjusting the central wavelength of said laser output to a first laser wavelength at or near a first absorption wavelength of a species being monitored;
   means for modulating said laser output about said first laser wavelength to establish a first modulated output having a first modulation frequency and a first modulation bandwidth and a second modulated output having said first modulation frequency and a second modulation bandwidth;
   means for providing said first and second modulated outputs to a sample being monitored;
   means for collecting at least some of said modulated outputs transmitted through said sample;
   means for determining an even harmonic of the collected outputs with respect to said first modulation frequency;
   means, responsive to said means for determining, for detecting from said even harmonic of said fist or said second modulated outputs the presence in said sample of said species being monitored; and
   means for resolving the concentration of the species being monitored by comparing said even harmonics of said collected outputs.

2. The gaseous species monitored of claim 1 in which said even harmonic is the second harmonic.

3. The gaseous species monitor of claim 1 in which one of said first and second modulation bandwidths is at least as large as the line width of the absorption line of said species being monitored.

4. The gaseous species monitors of claim 1 further including means for determining the line width of an absorption line of the species being monitored at the first absorption wavelength.

5. The gaseous species monitor of claim 4 in which said means for determining the line width includes means for comparing the even harmonics of said collected outputs.

6. The gaseous species monitor of claim 1 in which said means for adjusting includes a reference cell containing a reference absorber species.

7. The gaseous species monitor of claim 6 in which said reference absorber species is the species being monitored.

8. The gaseous species monitor of claim 6 in which said reference absorber species has an absorption line within one-half of said bandwidth of said first absorption wavelength.

9. The gaseous species monitor of claim 1 in which said laser means includes a semiconductor diode laser.

10. The gaseous species monitor of claim 9 in which said means for adjusting the wavelength of said laser output includes means for controlling the temperature of said laser means.

11. The gaseous species monitor of claim 9 in which said means for adjusting the wavelength of said laser output means includes means for controlling the current supplied to said laser means.

12. The gaseous species monitor of claim 1 further including means for determining the temperature of said sample.

13. The gaseous species monitor of claim 12 in which means for determining the temperature of said sample includes means for adjusting the central wavelength of said laser output to a second laser wavelength at or near a second absorption wavelength of the species being monitored.

14. The gaseous species monitor of claim 13 in which said means for determining the temperature of said sample further includes means for modulating said laser output about said second laser wavelength to establish a third modulated output having said first modulation frequency and said first modulation bandwidth.

15. The gaseous species monitor of claim 14 in which said means for determining the temperature of said sample further includes means for providing said third modulated output to said sample, means for collecting at least some of said third modulated output transmitted through said sample, and means for determining an even harmonic of the third collected output with respect to the modulation frequency.

16. The gaseous species monitor of claim 15 in which said means for determining the temperature of the sample further includes means for comparing the even harmonics of the collected outputs from said first and third modulated outputs.

17. The gaseous species monitor of claim 6 in which said means for adjusting further includes means for providing said first or second modulated output to said reference cell and means for collecting at least some of said first or second modulated output transmitted through said cell.

18. The gaseous species monitor of claim 17 in which said means for adjusting further includes means for determining an odd harmonic of the collected reference cell output with respect to said first modulation frequency.

19. The gaseous species monitor of claim 18 in which said means for adjusting further includes means for integrating said odd harmonic and providing the integrated odd harmonic as a drive signal to said laser means.

20. A wavelength-locked laser gaseous species monitor, comprising:
variable wavelength laser means for providing a laser output;
means for adjusting the central wavelength of said laser output alternately to a first laser wavelength at or near a first absorption wavelength of a species being monitored, and to a second laser wavelength at or near a second absorption wavelength of the species being monitored;
means for alternatively modulating said laser output about said first laser wavelength to establish a first modulated laser output having a first modulation frequency and first modulation bandwidth, and about said second laser wavelength to establish a second modulated laser output having said first modulation frequency and said first modulation bandwidth;
means for alternately providing said first and second modulated laser outputs to a sample being monitored;
means for collecting at least some of said modulated outputs transmitted through said sample;
means for determining an even harmonic of the collected outputs with respect to said first modulation frequency; and
means, responsive to said means for determining, for resolving the temperature of the sample being monitored by comparing the even harmonics of the collected outputs from said first and second modulated outputs.

21. The gaseous species monitor of claim 20 further including means, responsive to said means for determining an even harmonic, for calculating the concentration of the species being monitored.

22. A wavelength-locked laser gaseous species concentration monitor, comprising:
a variable wavelength semiconductor diode laser for providing a laser output;
means for supplying a drive current to said laser;
means for regulating the temperature of said laser;
means for driving said laser output to match the central wavelength of an absorption line of the species being monitored, said means for driving including:
means for modulating said laser output about a wavelength at or near said central wavelength at a known modulation frequency and bandwidth;
a reference cell containing the species being monitored;
means for passing said modulated laser output through said reference cell;
means for collecting at least some of said laser output transmitted through said reference cell;
means for determining the third harmonic of the collected reference cell output with respect to the modulation frequency; and
means responsive to said means for determining said third harmonic, for adjusting said laser drive current to adjust the laser output wavelength toward said central wavelength;
means for passing said modulated laser output through a gas sample being monitored;
means for collecting at least some of the laser output transmitted through said sample;
means for determining the second harmonic of the collected output from said sample with respect to the modulation frequency; and
means, responsive to said second harmonic, for determining the concentration of the species in said sample.

23. A wavelength-locked laser gaseous species absorption monitor comprising:
variable wavelength laser means for providing a laser output;
means for modulating said laser output about a central wavelength;

means for providing said modulated output to a sample being monitored and a reference volume containing the gaseous species being monitored;

means for collecting at least some of said modulated output transmitted through said sample and said reference volume;

means, responsive to said means for collecting and said means for modulating, for determining the third harmonic of the output collected from the reference volume;

means, responsive to said means for determining the third harmonic, for adjusting said central laser wavelength to decrease the absolute value of said third harmonic for locking said central wavelength on the center of an absorption line of the species being monitored;

means, responsive to said means for collecting and said means for modulating, for determining an even harmonic of the output collected from said sample; and means, responsive to said means for determining an even harmonic, for detecting from said even harmonic the presence in said sample of said species being monitored.

24. A wavelength-locked laser gaseous species monitor, comprising:

variable wavelength laser means for providing a laser output;

means for adjusting the central wavelength of said laser output alternately to a first laser wavelength at or near a first absorption wavelength of a species being monitored, and to a second laser wavelength at or near a second adsorption wavelength of the species being monitored;

means for alternately modulating said laser output about said first laser wavelength to establish a first modulated laser output having a first modulation frequency and first modulation bandwidth, and about said second laser wavelength to establish a second modulated laser output having said first modulation frequency and said first modulation bandwidth;

means for alternately providing said first and second modulated laser outputs to a sample being monitored;

means for collecting at least some of said modulated outputs transmitted through said sample;

means for determining an even harmonic of the collected outputs with respect to said first modulation frequency;

means, responsive to said means for determining, for resolving the temperature of the sample being monitored by comparing the even harmonics of the collected outputs from said first and second modulated outputs; and means, responsive to said means for determining, for detecting from at least one of said even harmonies the presence in said sample of said species being monitored.

* * * * *